(12) United States Patent
Nakata

(10) Patent No.: US 11,496,680 B2
(45) Date of Patent: Nov. 8, 2022

(54) IMAGING UNIT

(71) Applicant: SONY SEMICONDUCTOR SOLUTIONS CORPORATION, Kanagawa (JP)

(72) Inventor: Masashi Nakata, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 46 days.

(21) Appl. No.: 16/612,014

(22) PCT Filed: Jun. 8, 2018

(86) PCT No.: PCT/JP2018/022109
§ 371 (c)(1),
(2) Date: Nov. 8, 2019

(87) PCT Pub. No.: WO2019/003866
PCT Pub. Date: Jan. 3, 2019

(65) Prior Publication Data
US 2021/0144299 A1    May 13, 2021

(30) Foreign Application Priority Data
Jun. 27, 2017  (JP) .............................. JP2017-125092

(51) Int. Cl.
| | |
|---|---|
| *H04N 5/232* | (2006.01) |
| *G03B 30/00* | (2021.01) |
| *G02B 7/02* | (2021.01) |
| *H01L 27/146* | (2006.01) |
| *H04N 5/247* | (2006.01) |

(Continued)

(52) U.S. Cl.
CPC ......... *H04N 5/23238* (2013.01); *G02B 7/021* (2013.01); *G03B 30/00* (2021.01);
(Continued)

(58) Field of Classification Search
CPC ............... H04N 5/23238; H04N 5/247; H04N 5/23229; H01L 27/14627; H01L 27/14685;
(Continued)

(56) References Cited

U.S. PATENT DOCUMENTS 9,826,152 B1 * 11/2017  Martin .................... G02B 13/06
10,165,182 B1 * 12/2018  Chen .................... H04N 5/2258
(Continued)

FOREIGN PATENT DOCUMENTS

| | | |
|---|---|---|
| CN | 104365081 A | 2/2015 |
| CN | 105556383 A | 5/2016 |

(Continued)

OTHER PUBLICATIONS

International Search Report and Written Opinion of PCT Application No. PCT/JP2018/022109, dated Sep. 4, 2018, 10 pages of ISRWO.

*Primary Examiner* — Tat C Chio
(74) *Attorney, Agent, or Firm* — Chip Law Group

(57) ABSTRACT

Provided is an imaging unit that includes two or more imaging devices that are different from each other in imaging direction, and a substrate formed with each of the imaging devices. The substrate has a coupler formed between the imaging devices. The imaging unit including the plurality of imaging devices is able to yield a high-quality image when capturing an image of a wide range.

10 Claims, 16 Drawing Sheets

(51) Int. Cl.
*A61B 1/04* (2006.01)
*G02B 13/00* (2006.01)

(52) U.S. Cl.
CPC .... *H01L 27/1469* (2013.01); *H01L 27/14627* (2013.01); *H01L 27/14632* (2013.01); *H01L 27/14634* (2013.01); *H01L 27/14685* (2013.01); *H04N 5/23229* (2013.01); *H04N 5/247* (2013.01); *A61B 1/041* (2013.01); *G02B 13/0045* (2013.01)

(58) Field of Classification Search
CPC ........... H01L 27/14632; H01L 27/1469; H01L 27/14634; G02B 7/021; G02B 13/0045; G03B 30/00; A61B 1/041
See application file for complete search history.

(56) References Cited

U.S. PATENT DOCUMENTS

| | | | |
|---|---|---|---|
| 2013/0235149 A1* | 9/2013 | Tanaka | H04N 5/23238 348/36 |
| 2014/0192247 A1* | 7/2014 | Cheong | G06F 3/016 348/333.11 |
| 2015/0145952 A1 | 5/2015 | Hirata et al. | |
| 2016/0086379 A1 | 3/2016 | Sadi et al. | |
| 2016/0231641 A1 | 8/2016 | Minamisawa et al. | |
| 2018/0020160 A1* | 1/2018 | Lin | H04N 5/2252 |
| 2018/0139431 A1* | 5/2018 | Simek | H04N 5/2258 |

FOREIGN PATENT DOCUMENTS

| | | |
|---|---|---|
| JP | 2002-344811 A | 11/2002 |
| JP | 2004-015492 A | 1/2004 |
| JP | 2004-134875 A | 4/2004 |
| JP | 2005-175293 A | 6/2005 |
| JP | 2010-050702 A | 3/2010 |
| JP | 2010-276977 A | 12/2010 |
| KR | 10-2016-0062003 A | 6/2016 |
| TW | 201518850 A | 5/2015 |
| WO | 2013/186803 A1 | 12/2013 |
| WO | 2015/045791 A1 | 4/2015 |

\* cited by examiner

[ FIG. 1 ]
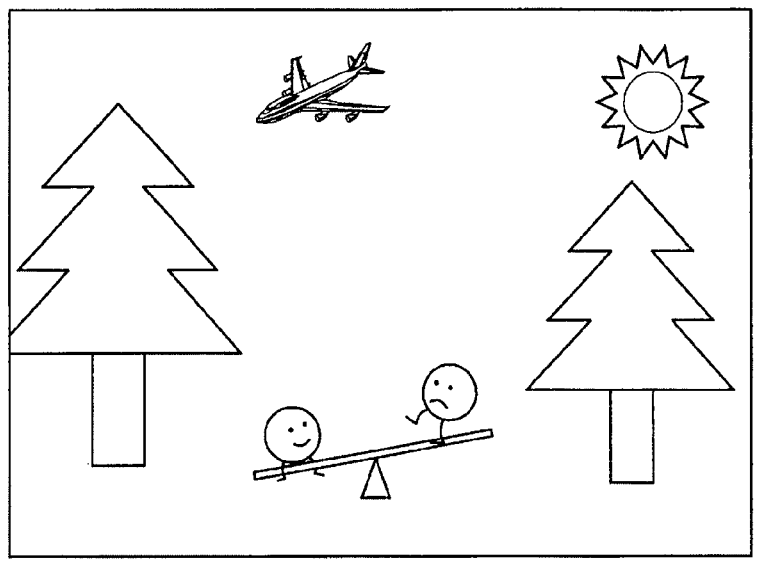
[ FIG. 2 ]
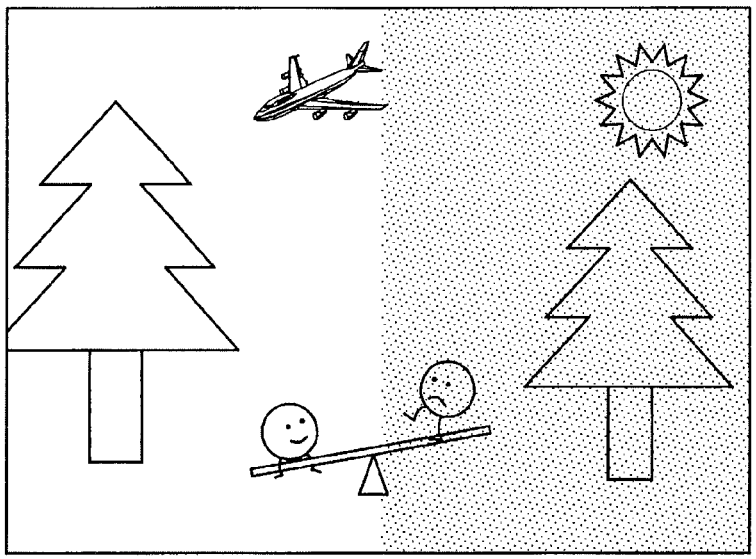

[FIG. 3]
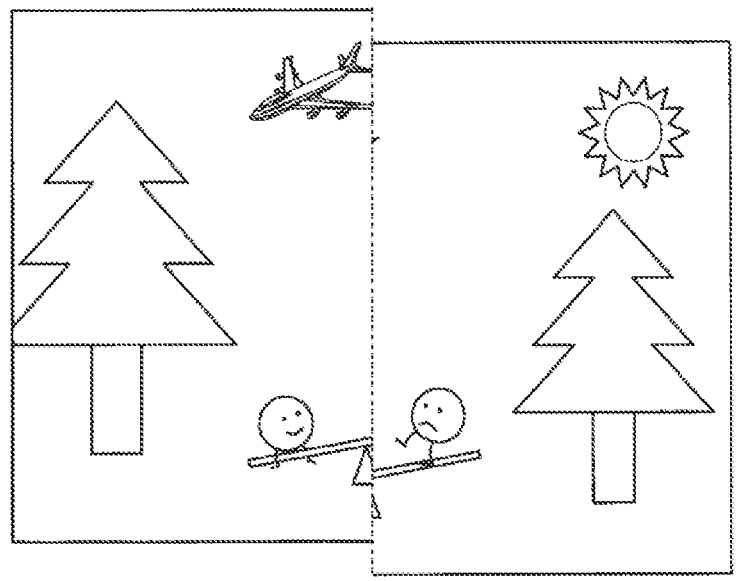
[FIG. 4]
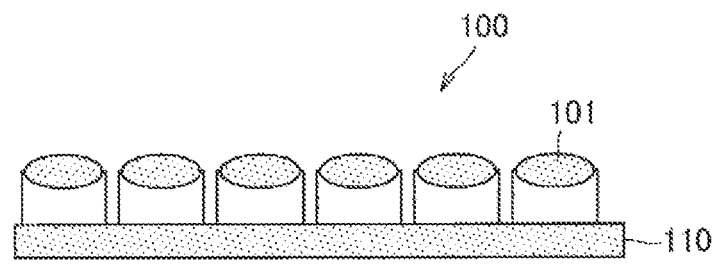
[FIG. 5]
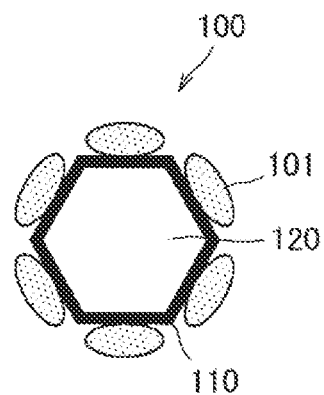

[ FIG. 6 ]
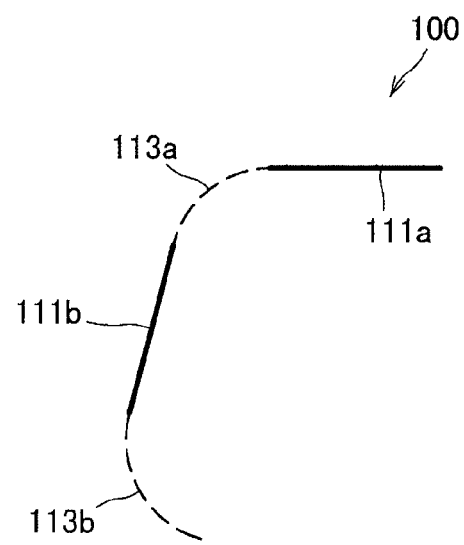
[ FIG. 7 ]
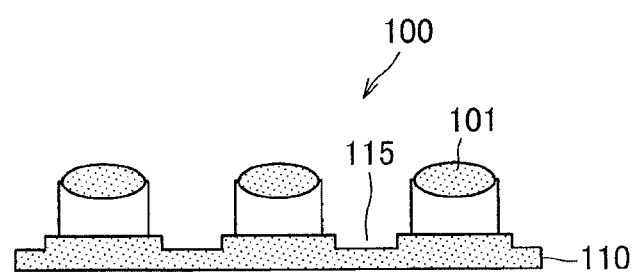

[FIG. 8]
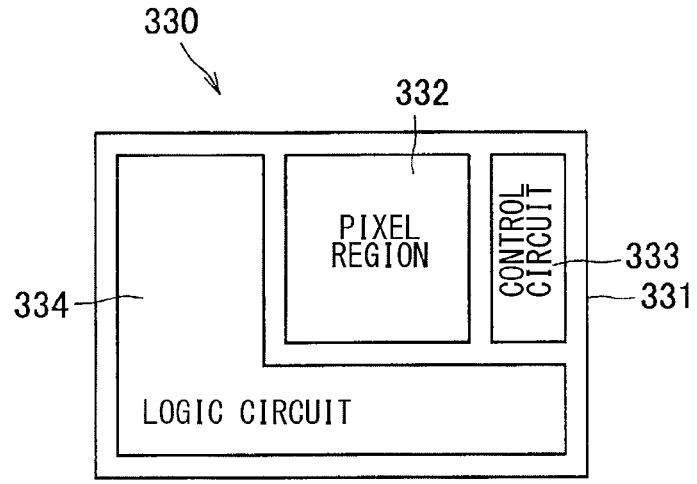
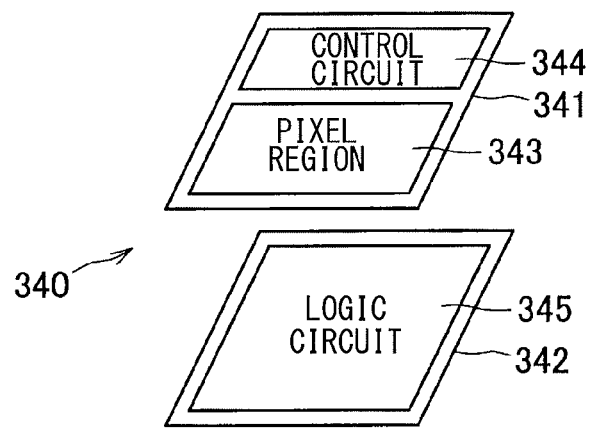
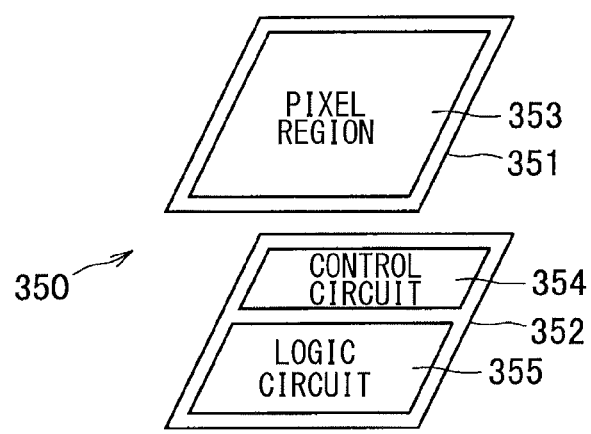

[ FIG. 9A ]
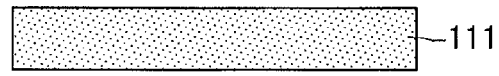
[ FIG. 9B ]
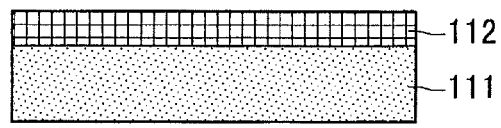
[ FIG. 9C ]
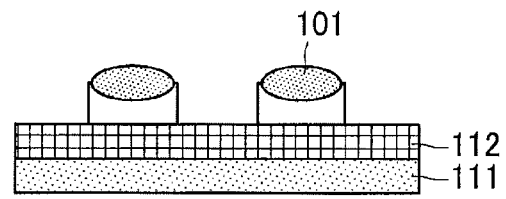
[ FIG. 9D ]
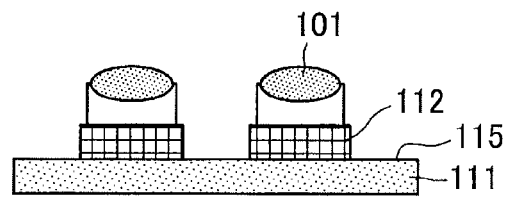
[ FIG. 10 ]
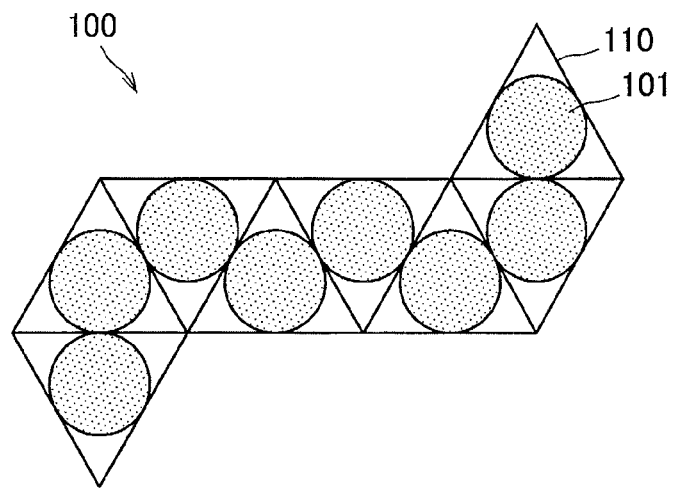

[ FIG. 11 ]
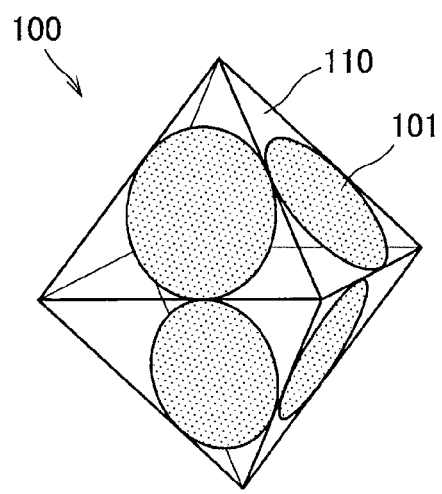

[FIG. 12A]
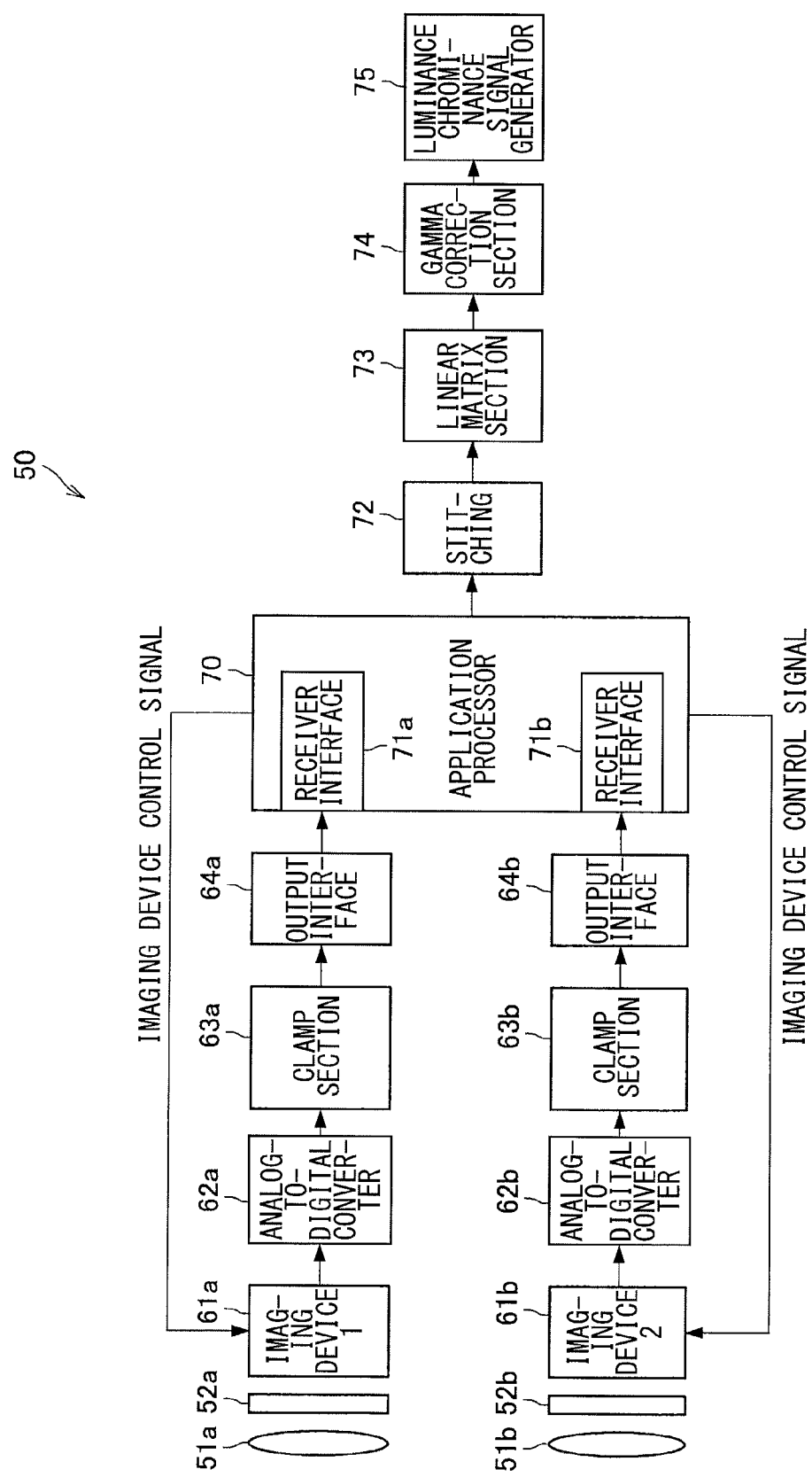

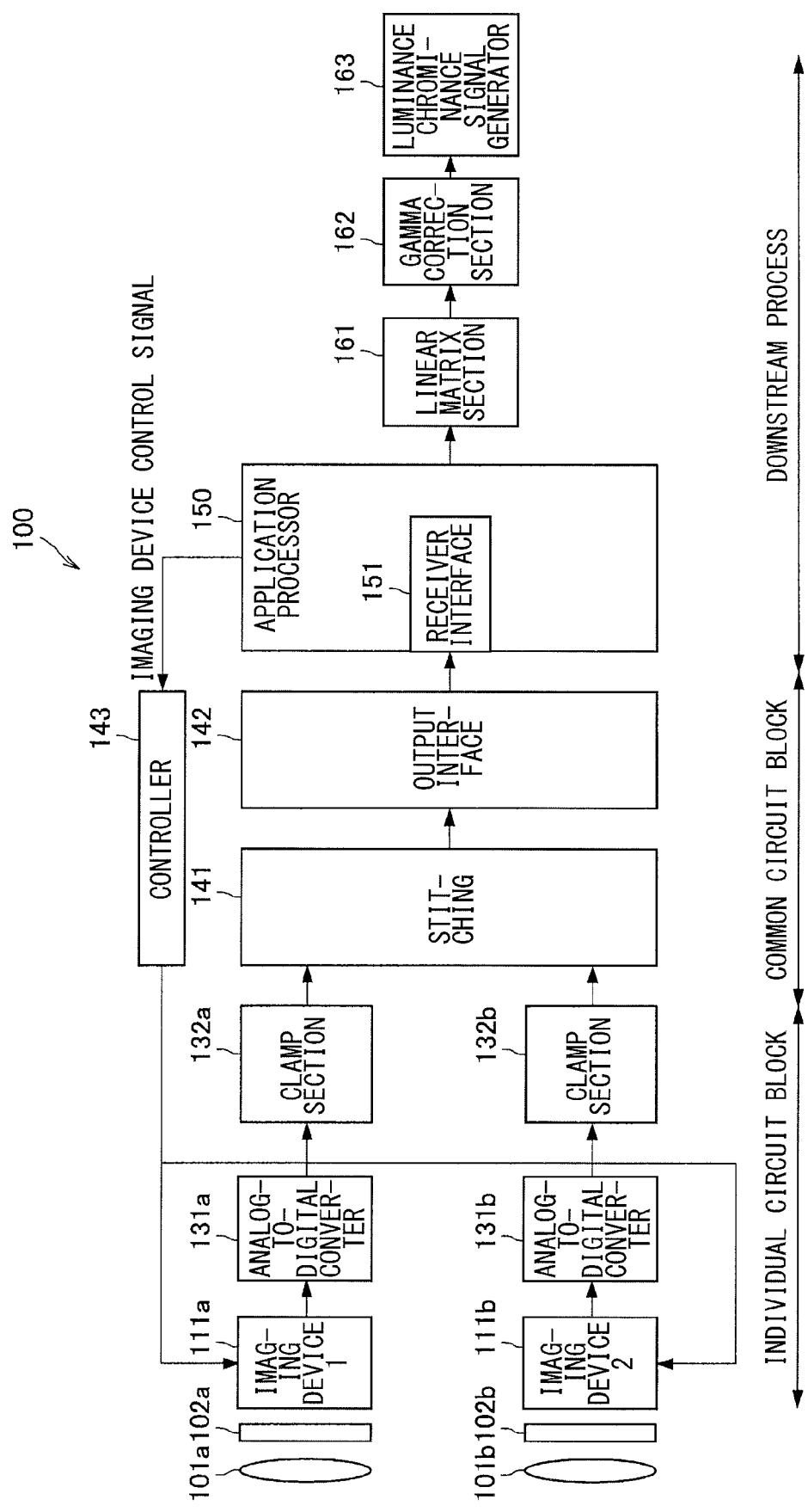
[FIG. 12B]

[FIG. 13]
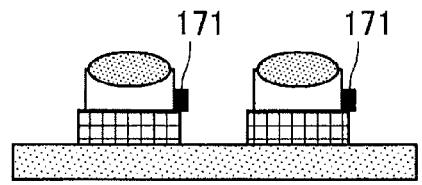
[FIG. 14]
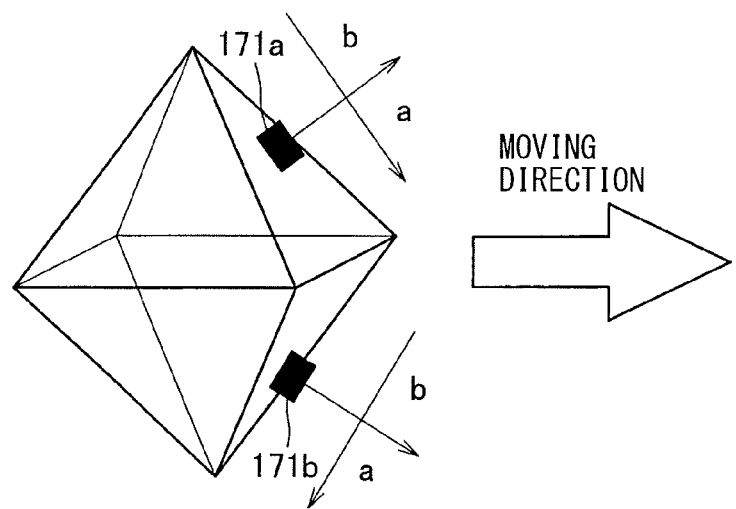
[FIG. 15]
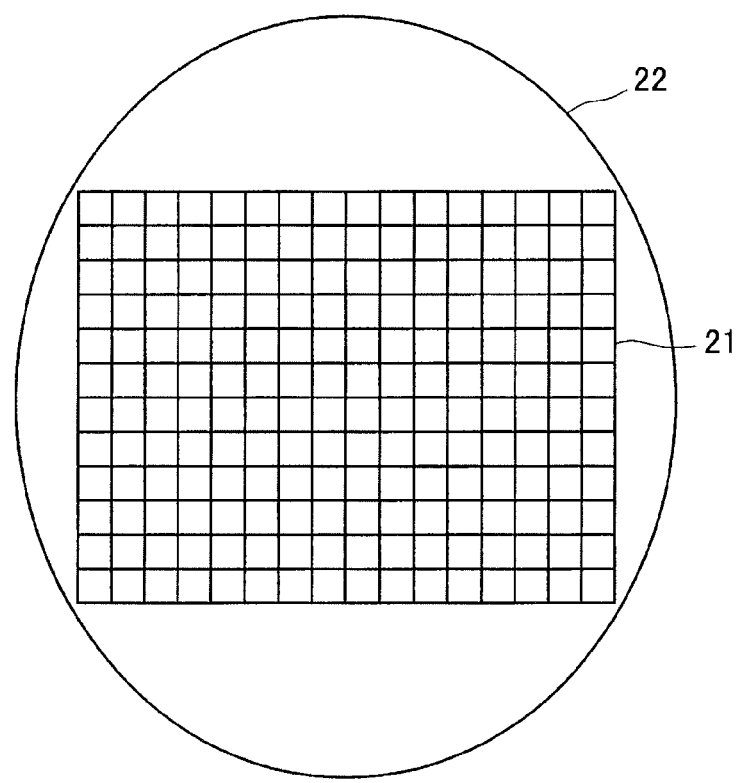

[ FIG. 16 ]
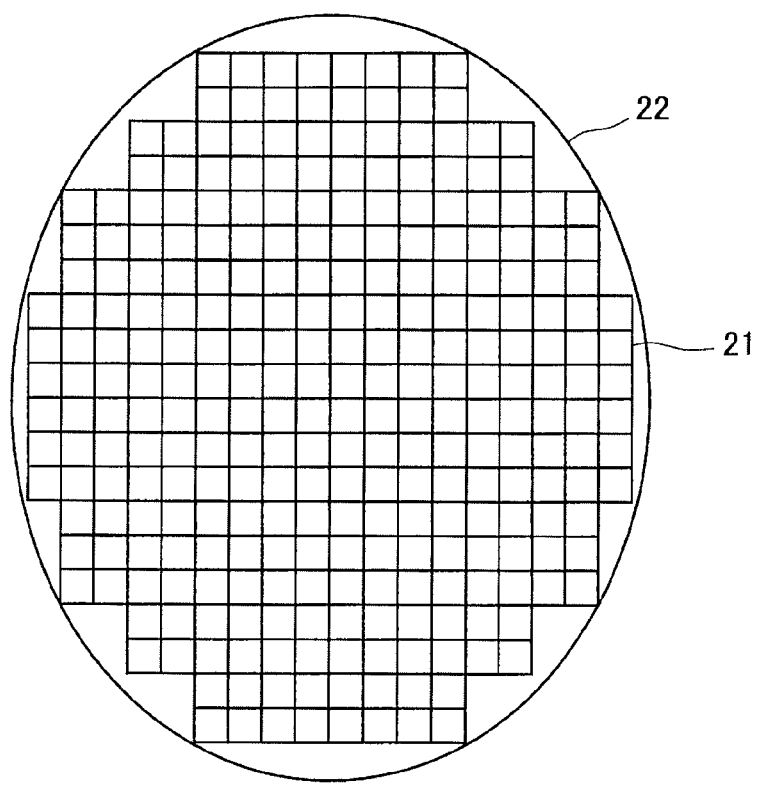

[ FIG. 17 ]
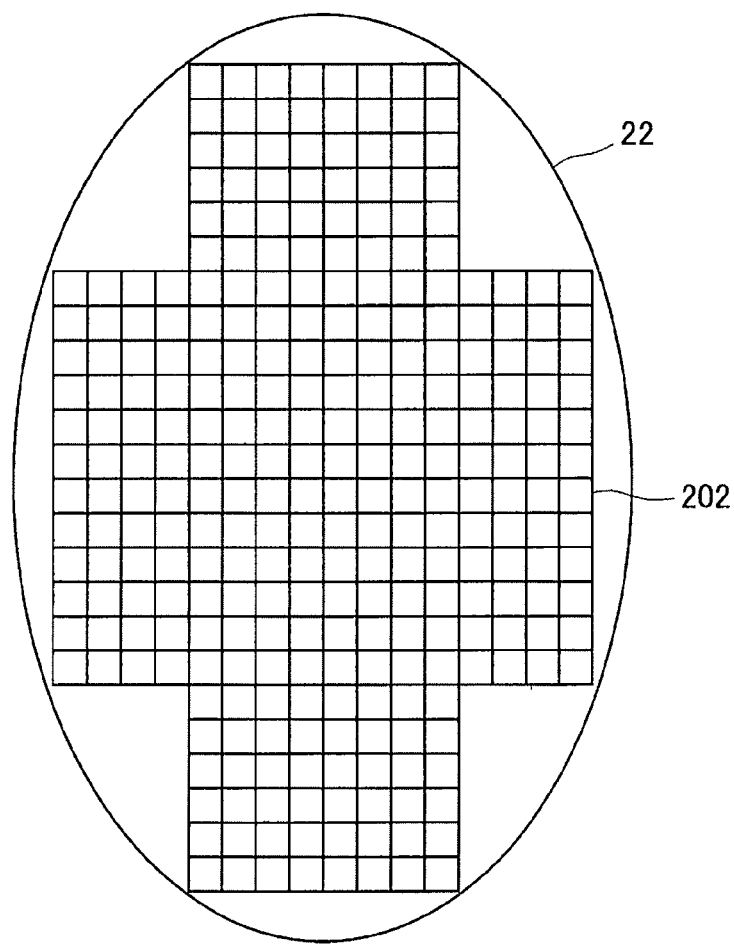

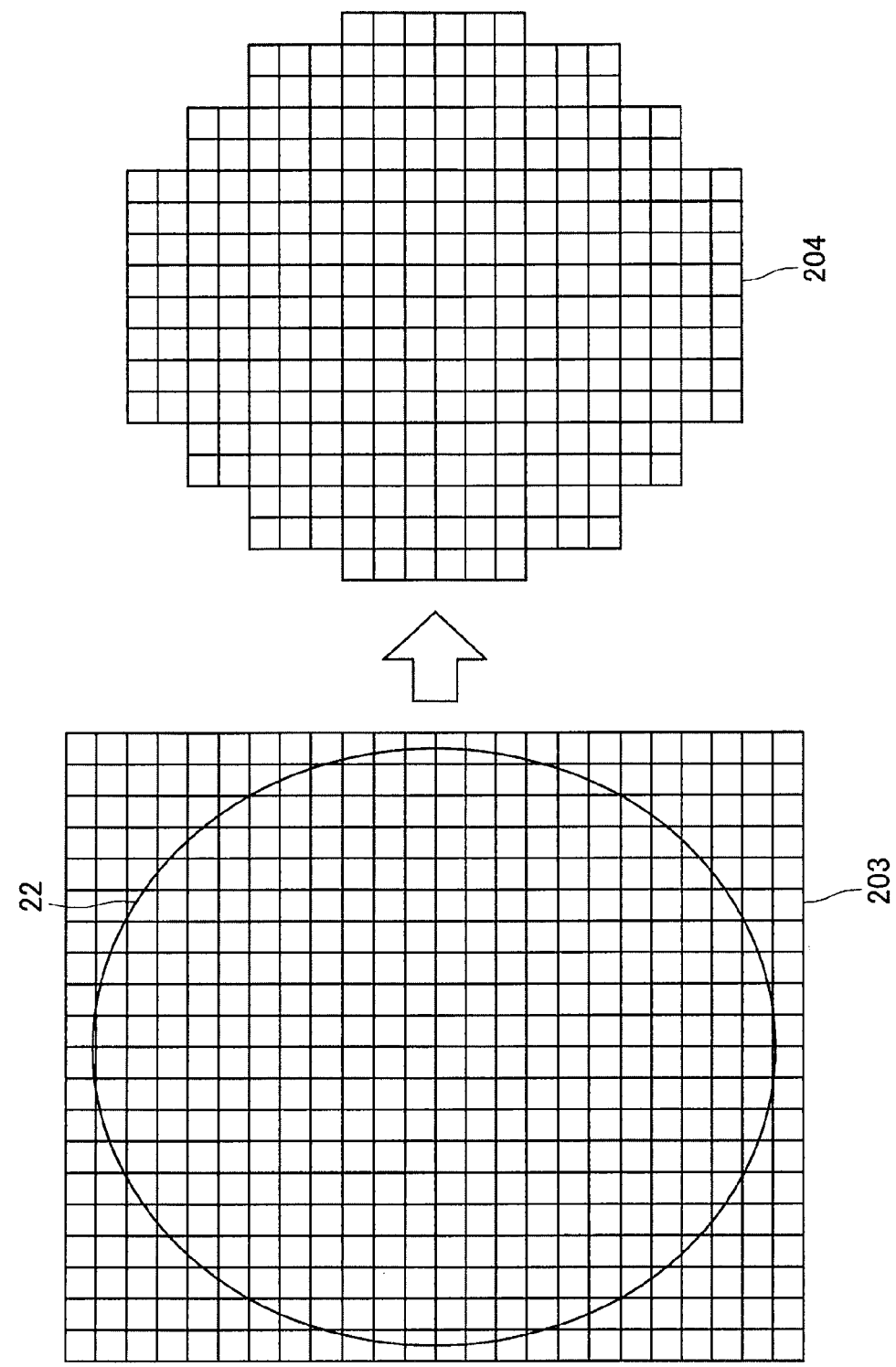
[FIG. 18]

[FIG. 19]
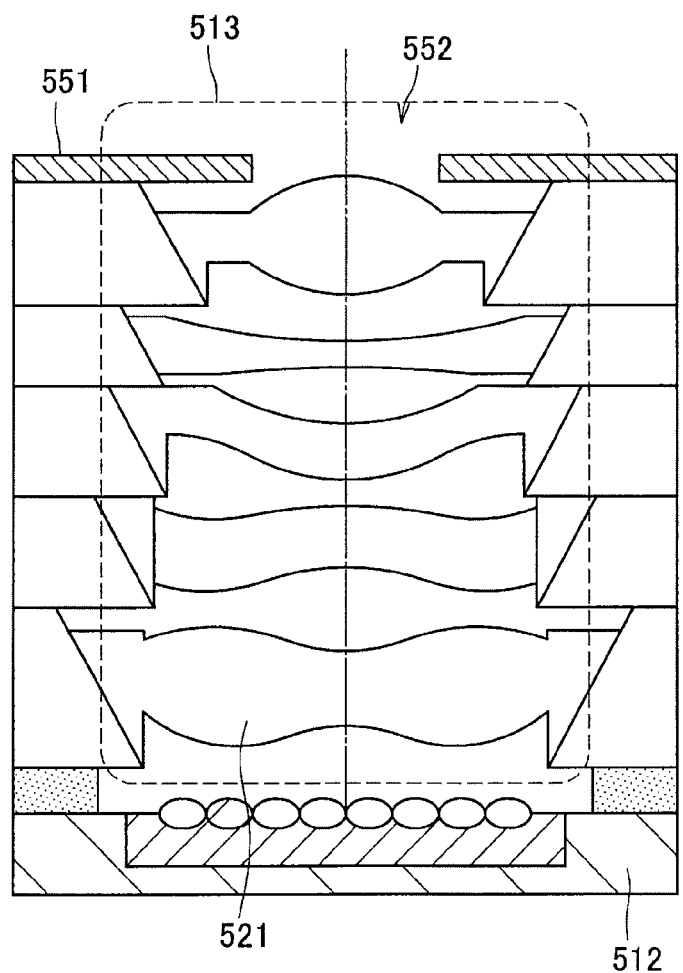

[ FIG. 20 ]
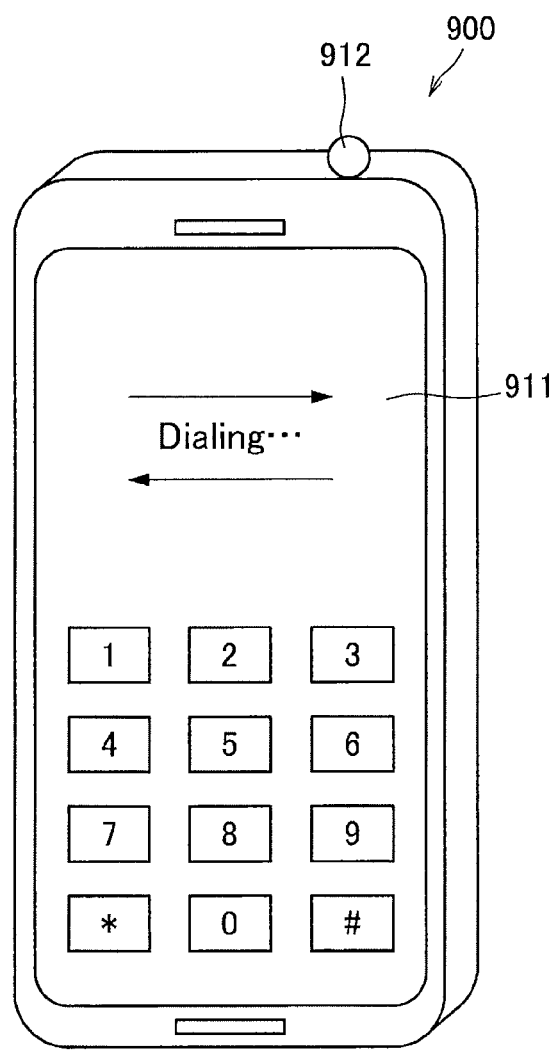

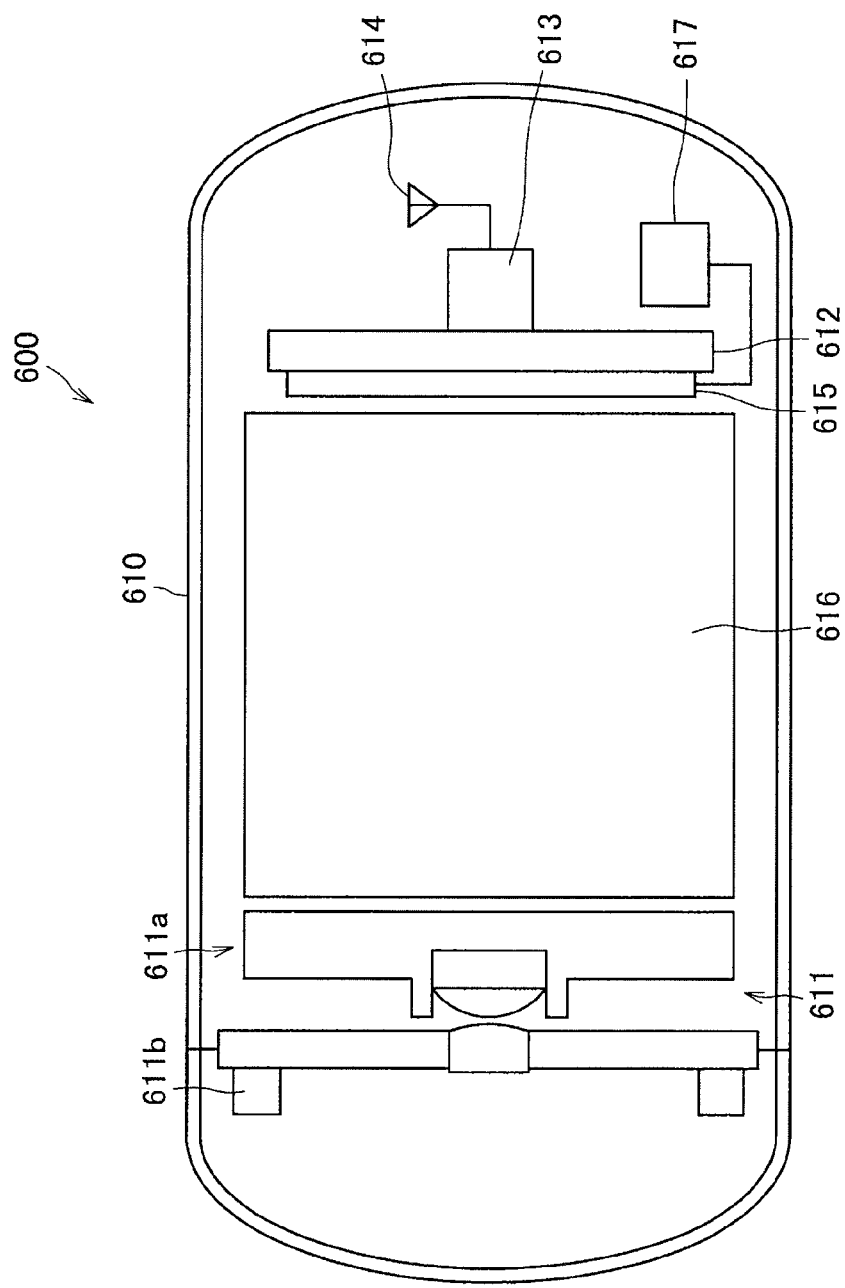
[FIG. 21]

[ FIG. 22 ]
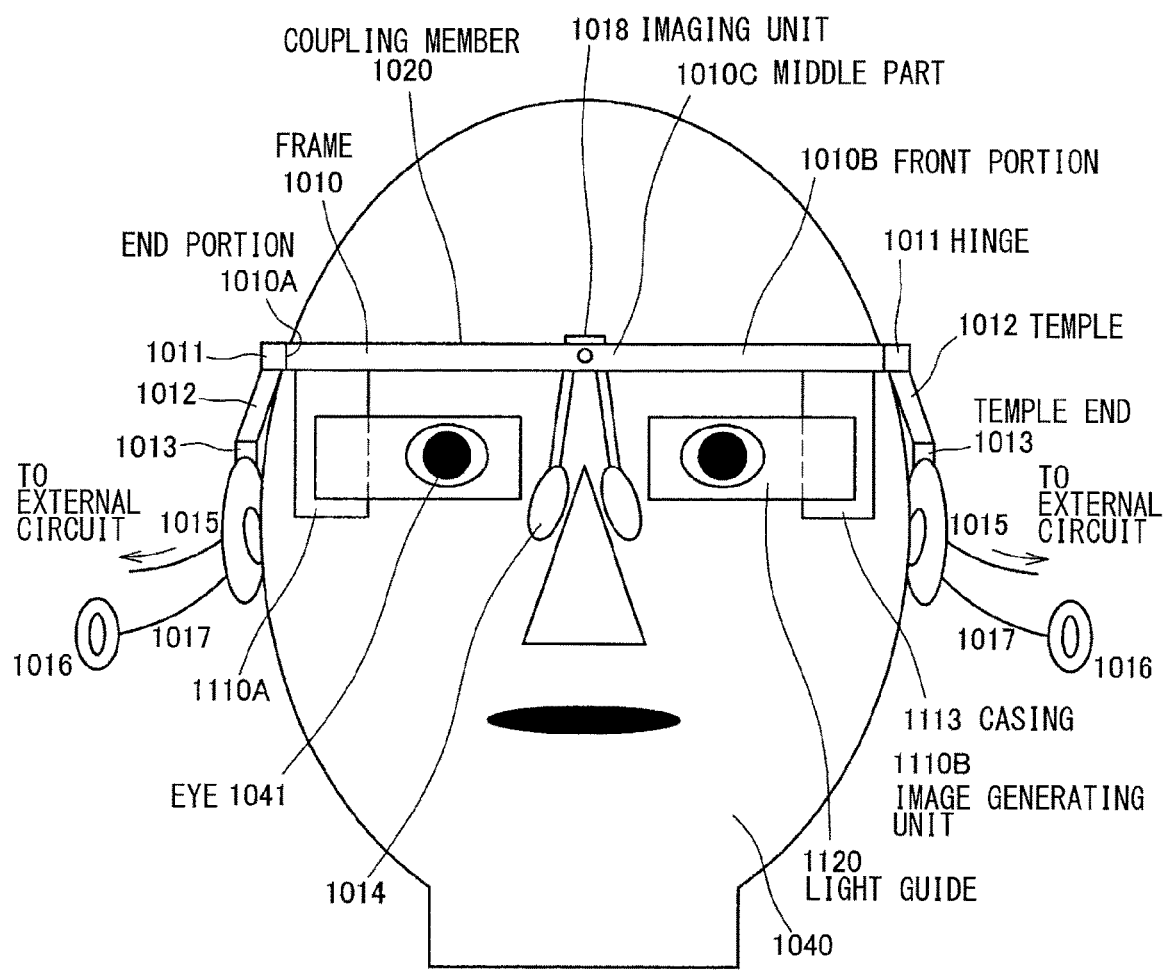

IMAGING UNIT

CROSS REFERENCE TO RELATED APPLICATIONS

This application is a U.S. National Phase of International Patent Application No. PCT/JP2018/022109 filed on Jun. 8, 2018, which claims priority benefit of Japanese Patent Application No. JP 2017-125092 filed in the Japan Patent Office on Jun. 27, 2017. Each of the above-referenced applications is hereby incorporated herein by reference in its entirety.

TECHNICAL FIELD

The present disclosure relates to an imaging unit.

BACKGROUND ART

A technique of an imaging unit is disclosed (for example, refer to PTL 1) that is able to perform imaging of a wide range such as a range of 180 degrees to 360 degrees using a plurality of imaging devices rather than imaging in one direction (hereinafter, such an imaging unit will also be referred to as "an omnidirectional camera").

CITATION LIST

Patent Literature

PTL 1: Specification of U.S. Unexamined Patent Application Publication No. 2016/0086379

SUMMARY OF THE INVENTION

Problems to be Solved by the Invention

However, due to using a plurality of imaging devices, an omnidirectional camera has some issues to be solved, such as an image quality difference due to variation in properties between the imaging devices, misalignment of images being combined due to production tolerance for placement of the imaging devices, and control of synchronization between the imaging devices.

The present disclosure therefore proposes a novel and improved imaging unit that includes a plurality of imaging devices to perform imaging of a wide range and that is able to yield a high-quality image through the imaging.

Means for Solving the Problems

The present disclosure provides an imaging unit that includes two or more imaging devices that are different from each other in imaging direction, and a substrate formed with each of the imaging devices, and having a coupler formed between the imaging devices.

Effects of the Invention

According to the present disclosure, as described above, it is possible to provide the novel and improved imaging unit that includes the plurality of imaging devices to perform imaging of a wide range and that is able to yield a high-quality image through the imaging.

It should be noted that the above-described effects are not necessarily limiting. Any of the effects indicated in this description or other effects that can be understood from this description may be exerted in addition to the above-described effects or in place of the above-described effects.

BRIEF DESCRIPTION OF DRAWING

FIG. 1 illustrates an example of a subject on which imaging is to be performed by an omnidirectional camera.

FIG. 2 is an explanatory diagram illustrating an example of a result of imaging of the subject illustrated in FIG. 1, by the omnidirectional camera.

FIG. 3 is an explanatory diagram illustrating an example of a result of imaging of the subject illustrated in FIG. 1, by the omnidirectional camera.

FIG. 4 is an explanatory diagram illustrating an example of external appearance of an imaging unit according to an embodiment of the present disclosure.

FIG. 5 is an explanatory diagram illustrating an example of the external appearance of the imaging unit according to the embodiment.

FIG. 6 is an explanatory diagram illustrating an enlarged view of a portion of the imaging unit with a silicon substrate wound around a support.

FIG. 7 is an explanatory diagram illustrating an example of the imaging unit whose imaging device is formed with recesses.

FIG. 8 is an explanatory diagram illustrating a basic general configuration of an imaging device.

FIG. 9A is an explanatory diagram illustrating a production step of the imaging unit according to the embodiment.

FIG. 9B is an explanatory diagram illustrating a production step of the imaging unit according to the embodiment.

FIG. 9C is an explanatory diagram illustrating a production step of the imaging unit according to the embodiment.

FIG. 9D is an explanatory diagram illustrating a production step of the imaging unit according to the embodiment.

FIG. 10 is an explanatory diagram illustrating an example of the imaging unit according to the embodiment.

FIG. 11 is an explanatory diagram illustrating an example of the imaging unit according to the embodiment.

FIG. 12A is an explanatory diagram illustrating an example of a functional configuration of an imaging unit for explaining a comparative example.

FIG. 12B is an explanatory diagram illustrating an example of the functional configuration of the imaging unit according to the embodiment.

FIG. 13 illustrates an example of the imaging devices in which lenses include gyroscope sensors.

FIG. 14 is an explanatory diagram illustrating an octahedral imaging unit with gyroscope sensors provided on respective surfaces of the octahedral imaging unit.

FIG. 15 is an explanatory diagram illustrating an example of an imaging region of a typical imaging device.

FIG. 16 is an explanatory diagram illustrating an example of an imaging region of each of imaging devices of the imaging unit according to the embodiment.

FIG. 17 is an explanatory diagram illustrating an example of the imaging region of each of the imaging devices of the imaging unit according to the embodiment.

FIG. 18 is an explanatory diagram illustrating an example of the imaging region of each of the imaging devices of the imaging unit according to the embodiment.

FIG. 19 is an explanatory diagram illustrating an example of a structure of a lens module according to the embodiment.

FIG. 20 is an explanatory diagram illustrating a smartphone in which the imaging unit according to the embodiment is mountable.

FIG. 21 is a diagram illustrating a cross-sectional configuration of a capsule endoscope to which the present technology has been applied.

FIG. 22 is an explanatory diagram illustrating a head-mounted display in which an imaging unit 100 according to an embodiment of the present disclosure is mountable.

MODES FOR CARRYING OUT THE INVENTION

The following describes a preferred embodiment of the present disclosure in detail with reference to the accompanying drawings. It should be noted that, in this description and the accompanying drawings, constituent elements that have substantially the same functional configuration are indicated by the same reference signs, and thus redundant description thereof is omitted.

It should be noted that the description is given in the following order.
1. Embodiment of Present Disclosure
    1.1. Circumstances
    1.2. Configuration Examples
2. Application Examples
3. Conclusion

1. FIRST EMBODIMENT

1.1. Circumstances

Before an embodiment of the present disclosure is described in detail, circumstances of the embodiment of the present disclosure are described.

As described above, a technique of an omnidirectional camera has been proposed that is able to perform imaging of a wide range such as a range of 180 degrees to 360 degrees using a plurality of imaging devices rather than imaging in one direction. The omnidirectional camera is able to yield an image of a wide range by combining images captured by the plurality of imaging devices.

However, due to using the plurality of imaging devices, the omnidirectional camera has many issues to be solved. One of the issues is an image quality difference due to variation in properties between the imaging devices. An image quality difference can for example occur in a case where a difference occurs in luminance between images captured by the imaging devices. FIG. 1 illustrates an example of a subject on which imaging is to be performed by an omnidirectional camera. In order to simplify explanation, the following discusses a case where imaging of the subject illustrated in FIG. 1 is performed using two imaging devices. FIG. 2 is an explanatory diagram illustrating an example of a result of the imaging of the subject illustrated in FIG. 1, by the omnidirectional camera. As seen in the drawing, variation in properties between the imaging devices can cause a difference in luminance. Variation in properties between the imaging devices can also cause other quality differences such as a difference in signal to noise ratio and a difference in color reproducibility, as well as a difference in luminance. When combining images, therefore, a process is to be performed for correcting such differences due to variation in properties between the imaging devices, making the image combining process time-consuming. Furthermore, imperfect correction adversely affects image quality.

The omnidirectional camera generates an image of a wide range by merging signals from the imaging devices. As such, production tolerance for placement of the imaging devices can cause image misalignment. FIG. 3 is an explanatory diagram illustrating an example of a result of imaging of the subject illustrated in FIG. 2, by the omnidirectional camera. As illustrated in FIG. 3, image misalignment can occur when signals from the imaging devices are merged, if the imaging devices are misaligned during placement thereof. It is necessary to perform alignment to solve the image misalignment before merging the signals, making the image combining process time-consuming. Furthermore, imperfect correction adversely affects image quality.

Moreover, due to including the plurality of imaging devices, the omnidirectional camera has an interface issue to be solved. The imaging devices are separate from each other, and therefore signals from the plurality of imaging devices are independently transmitted to an application processor. The application processor executes image processing such as merging (stitching) pieces of data transmitted from the plurality of imaging devices to generate an image of a wide range. The number of receivers (interfaces) necessary for receiving data from the imaging devices increases with an increase in the number of the imaging devices. Typically, the number of receivers for one application processor is limited due to specification constraints. Furthermore, increasing the number of receivers for an application processor increases production costs of the application processor.

Moreover, due to including the plurality of imaging devices, it is necessary for the omnidirectional camera to transmit an imaging instruction to each of the plurality of imaging devices. If the imaging devices are not synchronized in terms of execution timing of an imaging action, a difference occurs in imaging timing. This creates a delay in actual execution of an imaging process from transmission of the imaging instruction to each of the imaging devices, prolonging generation of an image of a wide range.

To address these, the discloser conducted extensive studies on a technique to solve the above-described issues in an imaging unit able to capture an image of a wide range. As a result, as described below, the discloser has solved the above-described issues and devised a technique that allows an imaging unit able to capture an image of a wide range to generate a high-quality image.

Description has been given above of circumstances in which the embodiment of the present disclosure has been achieved.

1.2. Configuration Examples

Next, specific examples of the imaging unit according to an embodiment of the present disclosure will be described. FIGS. 4 and 5 are explanatory diagrams each illustrating an example of external appearance of an imaging unit 100 according to the embodiment of the present disclosure. The following describes the imaging unit 100 according to the embodiment of the present disclosure using FIGS. 4 and 5.

The imaging unit 100 according to the embodiment of the present disclosure includes a plurality of lenses and a plurality of imaging devices in order to capture an image of a wide range, such as an all-direction image, at once. The imaging unit 100 according to the present embodiment has a configuration including the imaging devices formed on a single substrate (a silicon substrate) and the lenses formed on the imaging devices, rather than a configuration in which independently produced imaging devices are arranged. FIG. 4 illustrates a plurality of lenses 101 and an imaging device 110 formed on a silicon substrate. The silicon substrate may be a thin film and is bendable as long as a thickness thereof is approximately 200 μm. Desirably, the silicon substrate has a thickness of approximately 100 μm. Since the imaging devices are formed on the single silicon substrate, the extent of variation between the imaging devices such as described above is extremely small. The imaging unit 100 according to the embodiment of the present disclosure is therefore able to readily combine images captured by the plurality of imaging devices.

The imaging devices of the imaging unit 100 according to the embodiment of the present disclosure are electrically coupled to each other within the silicon substrate, thereby minimizing wire bonding. Thus, the imaging unit 100 according to the embodiment of the present disclosure allows reduction of undesired wiring lines and production of a small-sized omnidirectional camera. Furthermore, in the imaging unit 100 according to the embodiment of the present disclosure, a logic board is shared, allowing circuit area unused in each of the imaging devices to be effectively utilized between those imaging devices.

Besides, the imaging unit 100 according to the embodiment of the present disclosure is in an easily bendable structure because the imaging devices are formed on the thin silicon substrate. For example, FIG. 5 illustrates the imaging unit 100 having a structure in which the silicon substrate of the imaging devices 110 is wound around a support 120, which is a hexagonal prism. In the imaging unit 100 illustrated in FIG. 5, the silicon substrate is wound around the support 120, which is a hexagonal prism, with the lenses 101 positioned at surfaces of respective sides of the support 120. Such a structure enables the imaging unit 100 illustrated in FIG. 5 to capture an all-direction image. Furthermore, since the individual imaging devices of the imaging unit 100 illustrated in FIG. 5 are formed in an integrated manner while being arranged in series, it is possible to reduce the extent of variation in properties between the imaging devices and restrict misalignment thereof. Such a structure enables the imaging unit 100 illustrated in FIG. 5 to yield a high-quality all-direction image.

FIG. 6 is an explanatory diagram illustrating an enlarged view of a portion of the imaging unit 100 with the silicon substrate wound around the support 120 as illustrated in FIG. 5. The imaging device 110 includes imaging devices 111*a* and 111*b* respectively disposed on the surfaces of sides of the support 120. The imaging devices 111*a* and 111*b* have a coupler 113*a* therebetween, which is non-linear. The coupler 113*a* is for example curved as illustrated in FIG. 6. The imaging unit 100 also includes a coupler 113*b*, which is curved as illustrated in FIG. 6.

The couplers may be provided only with a wiring line or may be provided also with a circuit. Furthermore, data from the imaging devices may be output wirelessly or wired.

In order to facilitate winding of the imaging devices 110 around the support 120, recesses may be formed in the imaging device 110. FIG. 7 is an explanatory diagram illustrating an example of the imaging unit 100 whose imaging device 110 has recesses. For example, the imaging device 110 has a thickness of approximately 200 μm in portions having the lenses 101, and the imaging device 110 has a thickness of approximately 100 μm in portions having recesses 115.

Now, a basic general configuration of an imaging device that is used for the present technology will be described with reference to FIG. 8.

A top portion of FIG. 8 illustrates a solid-state imaging unit 330 as a first example of the imaging device that is used for the present technology. The solid-state imaging unit 330 includes a pixel region 332, a control circuit 333, and a logic circuit 334 mounted in a single semiconductor chip 331.

A middle portion of FIG. 8 illustrates a solid-state imaging unit 340 as a second example of the imaging device that is used for the present technology. The solid-state imaging unit 340 includes a first semiconductor chip section 341 and a second semiconductor chip section 342. A pixel region 343 and a control circuit 344 are mounted in the first semiconductor chip section 341. A logic circuit 345 is mounted in the second semiconductor chip section 342. The first semiconductor chip section 341 and the second semiconductor chip section 342 are then electrically coupled to each other, forming the solid-state imaging unit 340 as a single semiconductor chip.

A bottom portion of FIG. 8 illustrates a solid-state imaging unit 350 as a third example of the imaging device that is used for the present technology. The solid-state imaging unit 350 includes a first semiconductor chip section 351 and a second semiconductor chip section 352. A pixel region 353 is mounted in the first semiconductor chip section 351. A control circuit 354 and a logic circuit 355 are mounted in the second semiconductor chip section 352. The first semiconductor chip section 351 and the second semiconductor chip section 352 are then electrically coupled to each other, forming the solid-state imaging unit 350 as a single semiconductor chip.

More detailed production steps of the imaging unit 100 will be described using FIGS. 9A, 9B, 9C, and 9D. FIGS. 9A, 9B, 9C, and 9D are explanatory diagrams illustrating the production steps of the imaging unit 100 according to the embodiment of the present disclosure. First, as illustrated in FIG. 9A, a logic circuit board 111 including a control circuit, a logic circuit, an interface, and the like is manufactured. Next, as illustrated in FIG. 9B, an imaging device substrate 112 is bonded to the logic circuit board 111, and light condensing structures such as color filters and on-chip lenses are formed for respective pixels. The light condensing structures are not illustrated as being located within the imaging device substrate 112. Thereafter, the logic circuit board 111 having an unnecessary thickness is thinned by a process such as back-grinding and chemical mechanical polishing (CMP), and subsequently the lenses 101 are formed as illustrated in FIG. 9C. Lastly, as illustrated in FIG. 9D, the recesses 115 are formed by a process such as etching, dicing, and lasering.

Owing to the above-described production steps, the extent of variation between the imaging devices such as described above is extremely small. The imaging unit 100 according to the embodiment of the present disclosure is therefore able to readily combine images captured by the plurality of imaging devices.

Although FIG. 5 illustrates an example of the imaging unit 100 having a structure in which the imaging devices 110 are wound around the support 120, the present disclosure is not limited to such an example. The imaging unit 100 according to the embodiment of the present disclosure may take various forms to capture an image of a wide range.

For example, the logic circuit board 111, the imaging devices 110 including the imaging device substrate 112, and the lenses 101 may be formed such that the imaging unit 100 is constructed into an octahedron. FIGS. 10 and 11 are explanatory diagrams illustrating an example of the imaging unit 100 according to the embodiment of the present disclosure. FIG. 10 illustrates the imaging unit 100 in a flat state before being constructed. FIG. 11 illustrates the imaging unit 100 in an octahedron state after being constructed. The above-described configuration having the lenses 101 on the respective sides of the octahedron allows the imaging unit 100 to function as an omnidirectional camera able to capture an all-direction image.

The following first describes an example of a functional configuration of an imaging unit that is a comparative example, and then describes an example of a functional configuration of the imaging unit 100.

FIG. 12A is an explanatory diagram illustrating an example of a functional configuration of an imaging unit 50, which is a comparative example. The imaging unit 50 illustrated in FIG. 12A is a unit that generates an image of a wide range using imaging devices produced independently from each other. The following describes the example of the functional configuration of the imaging unit 50, which is a comparative example, using FIG. 12A.

In order to simplify explanation, FIG. 12A illustrating the imaging unit 50 illustrates only two optical systems each including a lens and an imaging device. As illustrated in FIG. 12A, the imaging unit 50 includes lenses 51a and 51b, infrared cut-off filters 52a and 52b, imaging devices 61a and 61b, analog-to-digital converters 62a and 62b, clamp sections 63a and 63b, output interfaces 64a and 64b, an application processor 70, a stitching section 72, a linear matrix section 73, a gamma correction section 74, and a luminance chrominance signal generator 75.

The imaging device 61a is irradiated with light having passed through the lens 51a and the infrared cut-off filter 52a that cuts off infrared regions. Likewise, the imaging device 61b is irradiated with light having passed through the lens 51b and the infrared cut-off filter 52b that cuts off infrared regions. The imaging devices 61a and 61b are for example complementary metal-oxide-semiconductor image sensors in which a plurality of unit pixels (also referred to below simply as "pixels") is two-dimensionally arranged in a matrix. The imaging devices 61a and 61b are not limited to complementary metal-oxide-semiconductor image sensors. Color filters in for example a Bayer array are provided over the respective unit pixels.

A pixel signal outputted from the imaging device 61a is converted from an analog signal to a digital signal through the analog-to-digital converter 62a. Likewise, a pixel signal outputted from the imaging device 61b is converted from an analog signal to a digital signal through the analog-to-digital converter 62b. The data from the analog-to-digital converter 62a and the data from the analog-to-digital converter 62b are subjected to black-level correction by the clamp sections 63a and 63b, and then sent to the application processor 70 through the output interfaces 64a and 64b, respectively. It should be noted that the imaging devices 61a and 61b may have a configuration incorporating an analog-to-digital converter.

The application processor 70 controls various operations related to an imaging process by the imaging unit 50. For example, the application processor 70 transmits, to the imaging devices 61a and 61b, an imaging device control signal to control an imaging process by the imaging devices 61a and 61b.

The application processor 70 includes two receiver interfaces 71a and 71b. The receiver interface 71a receives the data sent from the output interface 64a. The receiver interface 71b receives the data sent from the output interface 64b. The application processor 70 outputs the data received by the two receiver interfaces 71a and 71b to the stitching section 72 downstream of the application processor 70.

The stitching section 72 performs a process of merging the data sent from the application processor 70, which in other words is the data outputted from the clamp section 63a and the data outputted from the clamp section 63b. After the stitching section 72 has merged the data, the merged data is outputted to the linear matrix section 73.

The linear matrix section 73 performs a color reproduction process on the data outputted from the stitching section 72. The gamma correction section 74 performs a gamma correction process on the data outputted from the linear matrix section 73. The luminance chrominance signal generator 75 generates a luminance signal and a chrominance signal for the data outputted from the gamma correction section 74. The data outputted from the luminance chrominance signal generator 75 is outputted to outside (for example, to a display).

The imaging unit 50 illustrated in FIG. 12A generates an image of a wide range by combining data generated by the imaging devices 61a and 61b produced independently from each other. However, the imaging unit 50 illustrated in FIG. 12A has a production tolerance issue and a misalignment issue as described above due to the two imaging devices produced independently from each other. Furthermore, in order to receive data outputted from the respective imaging devices, it is necessary for the application processor 70 to be provided with receiver interfaces corresponding to the number of imaging devices. As described above, increasing the number of receivers for an application processor increases production costs of the application processor.

Next, an example of the functional configuration of the imaging unit 100 according to the embodiment of the present disclosure will be described. FIG. 12B is an explanatory diagram illustrating an example of the functional configuration of the imaging unit 100 according to the embodiment of the present disclosure. The following describes the example of the functional configuration of the imaging unit 100 according to the embodiment of the present disclosure using FIG. 12B.

In order to simplify explanation, FIG. 12B illustrating the imaging unit 100 illustrates only two optical systems each including a lens and an imaging device. As illustrated in FIG. 12B, the imaging unit 100 according to the embodiment of the present disclosure includes lenses 101a and 101b, infrared cut-off filters 102a and 102b, the imaging devices 111a and 111b, analog-to-digital converters 131a and 131b, clamp sections 132a and 132b, a stitching section 141, an output interface 142, a controller 143, an application processor 150, a linear matrix section 161, a gamma correction section 162, and a luminance chrominance signal generator 163.

The imaging device 111a is irradiated with light having passed through the lens 101a and the infrared cut-off filter 102a that cuts off infrared regions. Likewise, the imaging device 111b is irradiated with light having passed through the lens 101b and the infrared cut-off filter 102b that cuts off infrared regions. The imaging devices 111a and 111b are for example complementary metal-oxide-semiconductor image sensors in which a plurality of unit pixels is two-dimensionally arranged in a matrix. The imaging devices 111a and 111b are not limited to complementary metal-oxide-semiconductor image sensors. Color filters in for example a Bayer array are provided over the respective unit pixels.

A pixel signal outputted from the imaging device 111a is converted from an analog signal to a digital signal through the analog-to-digital converter 131a. Likewise, a pixel signal outputted from the imaging device 111b is converted from an analog signal to a digital signal through the analog-to-digital converter 131b. The thus converted data is subjected to black-level correction by the clamp sections 132a and 132b, and then sent to the stitching section 141. It should be noted that the imaging devices 111a and 111b may have a configuration incorporating an analog-to-digital converter.

The imaging device 111a to the clamp section 132a constitute a block where each individual optical system performs a process. This block is for example provided in the imaging device substrate 112 in the production processes described using FIGS. 9A, 9B, 9C, and 9D. This block is referred to as "an individual circuit block" in FIG. 12B.

The stitching section 141 merges data sent from the clamp section 132a and data sent from the clamp section 132b. Since the imaging devices of the imaging unit 100 according to the present embodiment are formed on a single silicon substrate as descried above, it is possible to significantly reduce variation in properties between the imaging devices and misalignment thereof. It is therefore possible for the imaging unit 100 according to the present embodiment to reduce the time for the merging process by the stitching section 141. Upon data merging by the stitching section 141, the merged data is outputted from the output interface 142 to the application processor 150. The output interface 142 may for example be an MIPI (Mobile Industry Processor Interface) compliant interface.

The controller 143 controls the imaging devices 111a and 111b for the imaging process. Specifically, the controller 143 performs overall control of the imaging devices 111a and 111b such as setting of an imaging timing and a light exposure period.

The stitching section 141, the output interface 142, and the controller 143 are common to all the optical systems, and are for example provided in the logic circuit board 111 in the production steps described using FIGS. 9A, 9B, 9C, and 9D. The stitching section 141, the output interface 142, and the controller 143 constitute a block referred to as "a common circuit block" in FIG. 12B.

The application processor 150 controls various operations related to the imaging process by the imaging unit 100. For example, the application processor 150 transmits, to the controller 143, an imaging device control signal to control the imaging process by the imaging devices 111a and 111b. That is, since the controller 143 is provided in the common circuit block, the controller 143 is able to send an instruction collectively to both of the imaging devices 111a and 111b.

That is, the imaging unit 100 according to the present embodiment bundles together communication systems for transmission of an instruction from the application processor 150 to all of the imaging devices. It should be noted that the communication systems as used herein refer to interfaces such as I2C (Inter-Integrated Circuit) interface or I3C interface. By bundling together communication systems for transmission of an instruction from the application processor 150 to all of the imaging devices, the imaging unit 100 according to the present embodiment is able to prevent a difference from occurring in imaging timing between the imaging devices, obtaining well-synchronized images from the respective imaging devices. As a result of obtaining well-synchronized images from the respective imaging devices, the imaging unit 100 according to the present embodiment is able to generate a high-quality image of a wide range.

Furthermore, the application processor 150 according to the present embodiment has a single receiver interface 151. The receiver interface 151 receives data sent from the output interface 142. Since the application processor 150 uses no more than one receiver to receive data of images captured by a plurality of optical systems, the present embodiment allows cost reduction for the application processor 150.

The linear matrix section 161 performs a color reproduction process on the data outputted from the application processor 150. The gamma correction section 162 performs a gamma correction process on the data outputted from the linear matrix section 161. The luminance chrominance signal generator 163 generates a luminance signal and a chrominance signal for the data outputted from the gamma correction section 162. The data output outputted from the luminance chrominance signal generator 138 is outputted to outside (for example, to a display).

The application processor 150, the linear matrix section 161, the gamma correction section 162, and the luminance chrominance signal generator 163 constitute a block referred to as a "downstream block" in FIG. 12B.

It should be noted that although the stitching section 141 of the imaging unit 100 illustrated in FIG. 12B is included in the "common circuit block", the present disclosure is not limited to such an example. The output interface 142 may output yet-to-be-merged data outputted from each of the imaging devices. The application processor 150 may then internally perform a process of generating an image of a wide range by combining images into one image.

The imaging unit 100 according to the present embodiment may be provided with gyroscope sensors within or in the vicinity of the respective imaging devices. FIG. 13 illustrates an example of the imaging unit 100 in which the lenses 101 include gyroscope sensors. As illustrated in FIG. 13, each of the lenses 101 is provided with a gyroscope sensor 171. Such a configuration enables the imaging unit 100 to grasp positional relationships between the individual imaging devices by referring to data outputted from each of the gyroscope sensors 171.

FIG. 14 is an explanatory diagram illustrating the octahedral imaging unit 100 with gyroscope sensors provided on respective surfaces of the octahedral imaging unit 100. In order to simplify explanation, FIG. 14 illustrates the imaging unit 100 by omitting the lenses 101. It should be noted that gyroscope sensors may be provided on all of the surfaces of the octahedron, although FIG. 14 illustrates only gyroscope sensors 171a and 171b. The size of the gyroscope sensors is not limited to that illustrated in FIG. 14, although the gyroscope sensors are illustrated as large for the convenience of explanation.

Since the gyroscope sensors are provided on the respective surfaces of the octahedron, the gyroscope sensors respectively detect different angles when the imaging unit 100 is moved. For example, when the imaging unit 100 is moved rightward as illustrated in FIG. 14, the gyroscope sensor 171a detects an amount of movement in terms of an "a" quadrant, while the gyroscope sensor 171b detects an amount of movement in terms of a "b" quadrant. The imaging unit 100 is able to determine positional relationships between the individual imaging devices by obtaining the amount of movement detected by each of the gyroscope sensors.

The information regarding the amount of movement detected by the gyroscope sensors is mutually recognized in the "common circuit block" in the imaging unit 100 illustrated in FIG. 12B. The imaging unit 100 according to the present embodiment then applies the information regarding the amount of movement detected by the gyroscope sensors to the process in the stitching section 141 thereby to achieve merging with less error.

Typically, an imaging device has an imaging region having a quadrilateral shape such as a rectangular shape and a square shape. In the imaging region, pixels are arranged in a matrix as described above. FIG. 15 is an explanatory diagram illustrating an example of the imaging region of a typical imaging device. The imaging unit has an imaging region 21 in which pixels are arranged in a quadrilateral shape (in a matrix). This is because a display device that displays a captured image is rectangular like a television and a smartphone. However, due to the imaging region being quadrilateral, a remaining region of the imaging device, which is not used for imaging, is large for a light condensing shape 22 of a corresponding lens.

For an image of a wide range such as an image that is captured by an omnidirectional camera, however, it is more important to take in as much space information as possible. Thus, it is unnecessary to put importance on the shape due to the camera being omnidirectional. For example, the imaging region may have a shape approximate to a circular or elliptical shape.

FIG. 16 is an explanatory diagram illustrating an example of an imaging region of each of the imaging devices of the imaging unit 100 according to the present embodiment. As illustrated in FIG. 16, each of the imaging devices of the imaging unit 100 may have an imaging region 201 having a shape approximate to a circular shape matching the light condensing shape of the corresponding lens. It should be noted that pixels are typically produced to have a square or rectangular shape. As such, the imaging region 201 is not to be a perfect circle, and is given a shape approximate to a circular shape by combining quadrilateral shapes. Thus, the region that is not used for imaging is reduced for the light condensing shape of the lens, allowing more space information to be taken in. It is necessary for the stitching, which is, for example, a process of merging signals from a plurality of imaging devices, to include regions overlapping between imaging devices when performing correction of image misalignment due to misalignment of the imaging devices. Expanding the imaging region enables use of information in the thus added region in the correction of image misalignment.

FIG. 17 is an explanatory diagram illustrating an example of the imaging region of each of the imaging devices of the imaging unit 100 according to the present embodiment. FIG. 17 illustrates an example of a case where each of the lenses has an elliptical light condensing shape 23 and each of the imaging devices has an imaging region 202 designed to match the elliptical light condensing shape 23.

Alternatively, the pixels themselves may be arranged in a square or rectangular shape in the imaging region in order to avoid complicated pixel signal reading, and only an effective portion that receives light from the lens may be used in subsequent signal processing (for example, stitching). FIG. 18 is an explanatory diagram illustrating an example of the imaging region of each of the imaging devices of the imaging unit 100 according to the present embodiment. As illustrated in FIG. 18, each of the imaging devices may have an imaging region 203 larger than the light condensing shape 22, and only a portion having the largest possible range within the light condensing shape, which in other words is an effective portion 204 that receives light from the corresponding lens, may be used in the process in the downstream stitching section 141.

FIG. 19 is an explanatory diagram illustrating an example of a configuration of a lens module according to the present embodiment. The lens module according to the present embodiment may have a configuration in which lenses are stacked on an imaging device. FIG. 19 illustrates an optical unit 513. The reference sign 512 represents a light receiving device. Light reaches the light receiving device 512 through a lens 521 including a plurality of lenses stacked on one another. The reference sign 551 represents an aperture plate, and the reference sign 552 represents an opening of the aperture plate 551. Needless to say, in the present disclosure, the configuration of the lens module is not limited to such an example.

2. APPLICATION EXAMPLES

The imaging unit 100 according to the embodiment of the present disclosure is mountable in various apparatuses. FIG. 20 is an explanatory diagram illustrating a smartphone 900 in which the imaging unit 100 according to the embodiment of the present disclosure is mountable. The smartphone 900 illustrated in FIG. 20 includes a display 911 and an imaging unit 912. By applying the above-described imaging unit including the plurality of imaging devices to the imaging unit 912, the smartphone 900 is enabled to yield high-quality image of a wide range.

FIG. 21 is a diagram illustrating a cross-sectional configuration of a capsule endoscope to which the present technology has been applied.

A capsule endoscope 600 includes, for example, a casing 610 having opposite semispherical end surfaces and a hollow cylindrical middle part, and includes within the casing 610, a camera (an ultraminiature camera) 611 that captures an image of the inside of a body cavity of a subject, memory 612 that records thereon image data of the image captured by the camera 611, and a wireless transmitter 613 that transmits the recorded image data to outside over an antenna 614 after the capsule endoscope 600 is discharged out of the subject.

Furthermore, CPU (Central Processing Unit) 615 and a coil (a magnetic force-current conversion coil) 616 are provided within the casing 610.

The CPU 615 controls capturing by the camera 611 and data accumulation to the memory 612. The CPU 615 also controls data transmission from the memory 612 to a data receiver (not illustrated) outside the casing 610 by the wireless transmitter 613. A coil 616 supplies power to the camera 611, the memory 612, the wireless transmitter 613, the antenna 614, and light sources 611b described below.

Furthermore, a magnetic (reed) switch 617 that detects setting of the capsule endoscope 600 to the data receiver is provided in the casing 610. The CPU 615 starts supplying power from the coil 616 to the wireless transmitter 613 once the reed switch 617 detects the setting to the data receiver and data transmission is enabled.

The camera 611 for example has an imaging device 611a and a plurality of (two in this example) light sources 611b. The imaging device 611a includes an objective optical system that captures an image of the inside of the body cavity. The plurality of light sources 611b illuminates the inside of the body cavity. Specifically, the camera 611 includes a device such as a complementary metal-oxide-semiconductor (CMOS) sensor and a charge-coupled device (CCD) including, for example, light-emitting diodes (LEDs) as the light sources 611b.

By applying the above-described imaging unit including the plurality of imaging devices to the camera 611, the capsule endoscope 600 is enabled to yield a high-quality image of a wide range.

For another application example, FIG. 22 is an explanatory diagram illustrating a head-mounted display in which the imaging unit 100 according to the embodiment of the present disclosure is mountable.

A frame 1010 includes a front portion 1010B that is disposed in front of an observer 1040, two temples 1012 pivotally attached to opposite ends of the front portion 1010B with hinges 1011, and temple ends (also referred to as end cells, earmuffs, or ear pads) 13 attached to tips of the respective temples 1012. A coupling member 1020 is attached to the front portion 1010B at a middle part 1010C (corresponding to a bridge of a typical eyewear) located between two eyes 1041 of the observer 1040. Nose pads 1014 are attached to a side of the coupling member 1020 that is opposed to the observer 1040. The frame 1010 and the coupling member 1020 each include a metal or plastic. The coupling member 1020 has a curved rod-like shape.

Furthermore, wiring lines (such as a signal line and a power line) 1015 extending from an image generating unit 111A run through the inside of the temples 1012 and the temple ends 1013, and then extend to outside from tips of the temple ends 1013. Furthermore, the image generating unit 1110A and an image generating unit 1110B each have an earphone 1016. Earphone wiring lines 1017 extending from the respective image generating units 1110A and 1110B run through the inside of the temples 1012 and the temple ends 1013, and then extend from the tips of the temple ends 1013 to the earphones 1016. More specifically, the earphone wiring lines 1017 extend from the tips of the temple ends 1013 to the earphones 1016 so as to run along back sides of pinnas (auricles) of ears. Such a configuration provides a neat head-mounted display without giving an impression that the earphones 1016 and the earphone wiring lines 1017 are untidily arranged. It should be noted that the reference sign 1012a represents covers of the temples, and the reference signs 1013a and 1013b represent components of the temple ends. Screws 1013c are used to assemble the components 1013a and 1013b of the temple ends.

Furthermore, an imaging unit 1018 including lenses and solid-state imaging devices, each of which is a CCD or a CMOS sensor, is attached to the middle part 1010C of the front portion 1010B (the solid-state imaging devices and the lenses are not illustrated). Specifically, the middle part 1010C has a through hole, and the coupling member 1020 has a recess at a location facing the through hole of the middle part 1010C. The imaging unit 18 is disposed within the recess. Light entering through the through hole of the middle part 1010C is condensed into the solid-state imaging devices by the lenses. Signals from the solid-state imaging devices are sent to the image generating unit 1110A through the wiring lines 1018a extending from the imaging unit 1018. It should be noted that the wiring lines 1018a run between the coupling member 1020 and the front portion 1010B, and are coupled to the image generating unit 1110A. Such a configuration makes it less noticeable that the head-mounted display incorporates the imaging unit.

By applying the imaging unit 100 according to the embodiment of the present disclosure to the imaging unit 1018, the head-mounted display illustrated in FIG. 22 is enabled to yield a high-quality image of a wide range.

Although three apparatuses are described herein as application examples, apparatuses to which the imaging unit 100 according to the embodiment of the present disclosure is applied are not limited to these examples. For example, the imaging unit 100 according to the embodiment of the present disclosure is applicable to other apparatuses such as single-lens reflex cameras, television cameras, and head-mounted display apparatuses that enable users to experience virtual reality (VR) or augmented reality (AR).

3. CONCLUSION

According to the embodiment of the present disclosure, as described above, it is possible to provide the imaging unit 100 able to capture an image of a wide range and generate a high-quality image. Since the imaging devices of the imaging unit 100 according to the embodiment of the present disclosure are formed in an integrated manner, it is possible to significantly reduce variation in properties between the imaging devices. This makes it possible for the imaging unit 100 according to the embodiment of the present disclosure to omit image processing or significantly reduce the time for image processing when generating an image of a wide range by combining a plurality of captured images.

Furthermore, since the imaging devices of the imaging unit 100 according to the embodiment of the present disclosure are formed in an integrated manner, it is possible to reduce image misalignment due to production tolerance for placement of the imaging devices. Since it is possible to reduce image misalignment due to production tolerance, the imaging unit 100 according to the embodiment of the present disclosure is able to perform calibration for correction of image misalignment and the merging process more readily and accurately.

Furthermore, the imaging unit 100 according to the embodiment of the present disclosure is able to merge data outputted from the plurality of imaging devices before outputting the data to the application processor. This makes it possible for the imaging unit 100 according to the embodiment of the present disclosure to provide the application processor with an image of a wide range without increasing the number of interfaces of the application processor.

Furthermore, the imaging unit 100 according to the embodiment of the present disclosure is able to send an imaging instruction collectively to the plurality of imaging devices. By sending an imaging instruction collectively to the plurality of imaging devices, It is possible to create a computer program that causes hardware such as CPU, ROM, and RAM incorporated in each unit to implement a function equivalent to that of the configuration of the unit described above. It is also possible to provide a storage medium recording such a computer program thereon. In addition, by constituting each of the functional blocks illustrated in the functional diagrams by hardware, it is also possible to allow a series of processes to be implemented by the hardware.

A preferred embodiment(s) of the present disclosure has/have been described above in detail with reference to the accompanying drawings, but the technical scope of the present disclosure is not limited to such an embodiment(s). It is apparent that a person having ordinary skill in the art of the present disclosure can arrive at various alterations and modifications within the scope of the technical idea described in the appended claims, and it is understood that such alterations and modifications naturally fall within the technical scope of the present disclosure.

Furthermore, the effects described herein are merely illustrative and exemplary, and not limiting. That is, the technique according to the present disclosure can exert other effects that are apparent to those skilled in the art from the description herein, in addition to the above-described effects or in place of the above-described effects.

It should be noted that the following configurations are also fall within the technical scope of the present disclosure.

(1)

An imaging unit including:

two or more imaging devices that are different from each other in imaging direction; and a substrate formed with each of the imaging devices, and having a coupler formed between the imaging devices.

(2)

The imaging unit according to (1), in which the coupler is non-linear.

(3)

The imaging unit according to (2), in which the coupler is curved.

(4)

The imaging unit according to any one of (1) to (3), including an output section that bundles outputs outputted from the plurality of imaging devices and outputs the bundled outputs.

(5)

The imaging unit according to any one of (1) to (4), including an image combiner that aligns outputs outputted from the plurality of imaging devices and merges the aligned outputs.

(6)

The imaging unit according to (1), including sensors that recognize directions of movement of the respective imaging devices.

(7)

The imaging unit according to (6), including an image combiner that aligns outputs outputted from the plurality of imaging devices and merges the aligned outputs, in which the image combiner merges the outputs using outputs outputted from the respective sensors.

(8)

The imaging unit according to any one of (1) to (7), in which the coupler is formed with a recess.

(9)

The imaging unit according to any one of (1) to (8), including a structure that includes the imaging devices stacked on the substrate.

(10)

The imaging unit according to any one of (1) to (9), in which the imaging devices each have pixels arranged in a quadrilateral shape.

(11)

The imaging unit according to any one of (1) to (9), in which the imaging devices each have pixels arranged in a circular shape.

REFERENCE SIGNS LIST

100: Imaging unit
101: Lens
101a: Lens
101b: Lens
110: Imaging device
111: Logic circuit board
111a: Imaging device
111b: Imaging device
112: Imaging device substrate
113a: Coupler
113b: Coupler
115: Recess
120: Support
171: Gyroscope sensor

The invention claimed is:

1. An imaging unit, comprising:
 a logic circuit board;
 a single substrate on the logic circuit board, wherein
  the single substrate includes a first surface and a second surface opposite to the first surface, and
  the logic circuit board is in contact with the second surface of the single substrate;
 at least two imaging devices, wherein
  each of the at least two imaging devices is on the first surface of the single substrate, and
  an imaging direction of a first imaging device of the at least two imaging devices is different from an imaging direction of a second imaging device of the at least two imaging devices; and
 a coupler between the first imaging device and the second imaging device, wherein the coupler comprises a recess between the first imaging device and the second imaging device.

2. The imaging unit according to claim 1, wherein the coupler is non-linear.

3. The imaging unit according to claim 2, wherein the coupler is curved.

4. The imaging unit according to claim 1, further comprising an output section configured to:
 bundle outputs from the at least two imaging devices; and
 output the bundled outputs.

5. The imaging unit according to claim 1, further comprising an image combiner configured to:
 align outputs from the at least two imaging devices; and
 merge the aligned outputs.

6. The imaging unit according to claim 1, further comprising at least two sensors configured to recognize a direction of movement of a respective imaging device of the at least two imaging devices.

7. The imaging unit according to claim 6, further comprising an image combiner configured to:
 align outputs from the at least two imaging devices; and
 merge, based on outputs from the at least two sensors, the aligned outputs.

8. The imaging unit according to claim 1, further comprising a structure that includes the at least two imaging devices stacked on the single substrate.

9. The imaging unit according to claim 1, wherein each of the at least two imaging devices has pixels in a quadrilateral shape.

10. The imaging unit according to claim 1, wherein each of the at least two imaging devices has pixels in a circular shape.

* * * * *